United States Patent [19]
Steiger et al.

[11] Patent Number: 5,483,960
[45] Date of Patent: Jan. 16, 1996

[54] MORPHOMETRIC X-RAY ABSORPTIOMETRY (MXA)

[75] Inventors: Peter Steiger, Framingham; Howard P. Weiss, Newton, both of Mass.

[73] Assignee: Hologic, Inc., Waltham, Mass.

[21] Appl. No.: 176,418

[22] Filed: Jan. 3, 1994

[51] Int. Cl.$^6$ ............................................. G06F 159/00
[52] U.S. Cl. .................... 128/653.1; 378/901; 378/54; 382/132
[58] Field of Search .................... 364/413.13, 413.22, 364/413.23, 413.26; 378/54, 55, 58, 56, 62, 146, 196, 89, 901; 128/653.1

[56] References Cited

U.S. PATENT DOCUMENTS

| | | | |
|---|---|---|---|
| 4,833,625 | 5/1989 | Fisher et al. | 395/139 |
| 5,040,199 | 8/1991 | Stein | 378/56 |
| 5,150,394 | 9/1992 | Karellas | 378/62 |
| 5,165,410 | 11/1992 | Warne et al. | 128/653.1 |
| 5,228,068 | 7/1993 | Mazess | 378/54 |
| 5,291,537 | 3/1994 | Mazess | 378/54 |
| 5,305,368 | 4/1994 | Bisek et al. | 378/146 |
| 5,306,306 | 4/1994 | Bisek et al. | 623/16 |

*Primary Examiner*—Gail O. Hayes
*Assistant Examiner*—Joseph Thomas
*Attorney, Agent, or Firm*—Cooper & Dunham

[57] ABSTRACT

MXA Scan analysis in accordance with an exemplary embodiment of the invention can be viewed as a process of placing points on the lateral morphometry image at the anterior, mid, and posterior positions of the inferior and superior endpoints for each vertebral body in the spinal region of interest. These point locations are then used to calculate the anterior, mid, and posterior heights of the vertebral bodies. These heights are then compared to one another and to known normal values for the heights and ratios of the heights for each vertebral body and among vertebral bodies to quantify the degree of vertebral deformity.

26 Claims, 10 Drawing Sheets

Microfiche Appendix Included
(153 Microfiche, 2 Pages)

```
A08119304  Wed 11.Aug.1993      09:44
Name:                             BT
Comment:
I.D.:                      Sex:    F
S.S.#         - -          Ethnic:  C
ZIP Code:                  Height:5'10"
Scan Code:                 Weight:  130
BirthDate: 14.July.78      Age:    15
Physician:         TESINI
      Image not for diagnostic use
   SD: 1mm     1mm     1mm    0.05  0.05
        PH      MH      AH   WEDGE MWEDGE
       (mm)    (mm)    (mm)
  T4   21.1    19.5    17.2   0.81  0.92
  T5   20.0    18.4    16.7   0.83  0.92
  T6   21.7    20.1    18.0   0.83  0.93
  T7   21.4    19.8    18.0   0.84  0.92
  T8   21.4    20.1    18.8   0.88  0.94
  T9   21.7    20.6    19.4   0.89  0.95
 T10   23.3    22.2    21.0   0.90  0.95
 T11   25.2    23.0    21.5   0.85  0.91
 T12   26.6    24.6    23.1   0.87  0.92
  L1   28.0    26.0    24.8   0.88  0.93
  L2   28.1    26.3    25.9   0.92  0.94
  L3   27.5    26.8    27.0   0.98  0.98
  L4   28.0    27.1    27.0   0.96  0.97
```

```
A08119304  Wed 11.Aug.1993  09:44
Name:                              BT
I.D.:                     Sex:     F
BirthDate: 14.July.78     Age:    15
```

Image not for diagnostic use

| SD: | 1mm PH (mm) | 1mm MH (mm) | 1mm AH (mm) | 0.05 WEDGE | 0.05 MWEDGE |
|---|---|---|---|---|---|
| T4  | 21.1 | 19.5 | 17.2 | 0.81 | 0.92 |
| T5  | 20.0 | 18.4 | 16.7 | 0.83 | 0.92 |
| T6  | 21.7 | 20.1 | 18.0 | 0.83 | 0.93 |
| T7  | 21.4 | 19.8 | 18.0 | 0.84 | 0.92 |
| T8  | 21.4 | 20.1 | 18.8 | 0.88 | 0.94 |
| T9  | 21.7 | 20.6 | 19.4 | 0.89 | 0.95 |
| T10 | 23.3 | 22.2 | 21.0 | 0.90 | 0.95 |
| T11 | 25.2 | 23.0 | 21.5 | 0.85 | 0.91 |
| T12 | 26.6 | 24.6 | 23.1 | 0.87 | 0.92 |
| L1  | 28.0 | 26.0 | 24.8 | 0.88 | 0.93 |
| L2  | 28.1 | 26.3 | 25.9 | 0.92 | 0.94 |
| L3  | 27.5 | 26.8 | 27.0 | 0.98 | 0.98 |
| L4  | 28.0 | 27.1 | 27.0 | 0.96 | 0.97 |

Spinal Deformity Index (Minne)

|     | SDI(Ha) | SDI(Hm) | SDI(Hp) | TOTAL |
|---|---|---|---|---|
| T4  | --.-- | --.-- | --.-- | --.-- |
| T5  | --.-- | --.-- | 0.01  | 0.01  |
| T6  | --.-- | --.-- | --.-- | --.-- |
| T7  | --.-- | --.-- | --.-- | --.-- |
| T8  | --.-- | --.-- | --.-- | --.-- |
| T9  | --.-- | --.-- | --.-- | --.-- |
| T10 | --.-- | 0.04  | --.-- | 0.04  |
| T11 | --.-- | 0.04  | --.-- | 0.04  |
| T12 | --.-- | 0.03  | --.-- | 0.03  |
| L1  | --.-- | 0.05  | --.-- | 0.05  |
| L2  | --.-- | 0.02  | 0.02  | 0.04  |
| L3  | --.-- | --.-- | --.-- | --.-- |
| L4  | --.-- | --.-- | --.-- | --.-- |
| TOT | --.-- | 0.18  | 0.03  | 0.21  |

Vertebral Deformity (McCloskey)

|     | Ant | Cent | Post | Crush | Total |
|---|---|---|---|---|---|
| T4  | -- | -- | -- | -- | 0 |
| T5  | -- | -- | -- | -- | 0 |
| T6  | -- | -- | -- | -- | 0 |
| T7  | -- | -- | -- | -- | 0 |
| T8  | -- | -- | -- | -- | 0 |
| T9  | -- | -- | -- | -- | 0 |
| T10 | -- | -- | -- | -- | 0 |
| T11 | -- | -- | -- | -- | 0 |
| T12 | -- | -- | -- | -- | 0 |
| L1  | -- | -- | -- | -- | 0 |
| L2  | -- | -- | -- | -- | 0 |
| L3  | -- | -- | -- | -- | 0 |
| L4  | -- | -- | -- | -- | 0 |
| TOT | 0  | 0  | 0  | 0  | 0 |

FIG. 9

```
A08119304   Wed 11.Aug.1993 09:44
Name:                           BT
Comment:
I.D.:                    Sex:   F
S.S.#            - -     Ethnic: C
ZIP Code:                Height:5'10"
Scan Code:               Weight:  130
BirthDate: 14.July.78    Age 15
Physician:         TESINI
       Image not for diagnostic use
Vertebral Deformity (McCloskey)
       Ant   Cent   Post  Crush Total
```

|     | Ant  | Cent | Post | Crush | Total |
|-----|------|------|------|-------|-------|
| T4  | ---  | ---  | ---  | ---   | 0     |
| T5  | ---  | ---  | ---  | ---   | 0     |
| T6  | ---  | ---  | ---  | ---   | 0     |
| T7  | ---  | ---  | ---  | ---   | 0     |
| T8  | ---  | ---  | ---  | ---   | 0     |
| T9  | ---  | ---  | ---  | ---   | 0     |
| T10 | ---  | ---  | ---  | ---   | 0     |
| T11 | ---  | ---  | ---  | ---   | 0     |
| T12 | ---  | ---  | ---  | ---   | 0     |
| L1  | ---  | ---  | ---  | ---   | 0     |
| L2  | ---  | ---  | ---  | ---   | 0     |
| L3  | ---  | ---  | ---  | ---   | 0     |
| L4  | ---  | ---  | ---  | ---   | 0     |
| TOT | 0    | 0    | 0    | 0     | 0     |

FIG. 10

```
A08119304    Wed 11.Aug.1993      09:44
Name:                                  BT
Comment:
I.D.:                        Sex:       F
S.S.#             --  --     Ethnic:    C
ZIP Code:                    Height:5'10"
Scan Code:                   Weight:  130
BirthDate: 14.July.78        Age:     15
Physician:              TESINI
        Image not for diagnostic use
        Spinal Deformity Index (Minne)
        SDI(Ha)  SDI(Hm)  SDI(Hp)   TOTAL
T4      --.--    --.--    --.--     --.--
T5      --.--    --.--     0.01      0.01
T6      --.--    --.--    --.--     --.--
T7      --.--    --.--    --.--     --.--
T8      --.--    --.--    --.--     --.--
T9      --.--    --.--    --.--     --.--
T10     --.--    --.--    --.--     --.--
T11     --.--     0.04    --.--      0.04
T12     --.--     0.04    --.--      0.04
L1      --.--     0.03    --.--      0.03
L2      --.--     0.05    --.--      0.05
L3      --.--     0.02     0.02      0.04
L4      --.--    --.--    --.--     --.--
TOT     --.--     0.18     0.03      0.21
```

MORPHOMETRIC X-RAY ABSORPTIOMETRY (MXA)

REFERENCE TO MICROFICHE APPENDIX

The present application incorporates a microfiche appendix with two sheets of microfiche having 153 frames.

BACKGROUND OF THE INVENTION

The invention is in the field of imaging using penetrating radiation and pertains in particular to obtaining and processing penetrating radiation measurements and especially to morphometric x-ray absorptiometry referred to by the acronym MXA.

In fields such as the diagnosis of osteoporosis, it can be desirable to confirm a fracture associated with low bone material density, such as a hip, wrist or vertebral fracture [1]. (Numbers in square brackets refer to items which are listed in a bibliography at the end of the specification and are hereby incorporated by reference). Lateral thoracic and lumbar spine films have been utilized for the diagnosis of vertebral fractures in order to confirm crush and wedge deformities of vertebral bodies in the range encompassing T4 and L4 vertebrae. A number of studies have evaluated methods for the identification of vertebral fractures by vertebral morphometry and the correlation thereof with readings of radiologists [2, 3, 4, 5, 6, 7, 8, 9]. Some vertebral morphometry techniques involve digitizing conventional radiograms (x-ray films) and obtaining anterior, posterior and mid-vertebral heights. However, there can be disadvantages in this approach such as operator imprecision in placing the points for digitization on the radiograms, the use of multiple exposures to image both thoracic and lumbar regions of the spine due to the relatively large attenuation difference between the thoracic and lumbar areas, the possible need for retakes, and the radiation dose that can be associated with this procedure (such as 900 mRem without repeat exposures). In addition, geometric distortion can be a factor in using such digitized conventional x-ray films because they typically are obtained using cone beam geometry. As a result of such geometric distortion, different points in the radiogram are magnified and distorted in relative position in different ways. For example, areas closer to the edge of the film image are magnified more and are viewed at a somewhat oblique angle, whereas areas close to the center are magnified less and are viewed at an angle closer to perpendicular. Still in addition, the identification of vertebral levels can be difficult and film handling and archiving can involve considerable overhead. Rectilinear scanning, using a bone densitometer with a thin pencil beam of x-rays can counter the geometric distortion problem but can introduce the disadvantage of a much longer scanning time to acquire the necessary x-ray data. The use of a fan beam CT scanner in a scout view mode can decrease the scanning time as compared with rectilinear scanning. See W. A. Kalender, et al., Determination of Geometric Parameters and Osteoporosis Indices for Lumbar Vertebrae from Lateral QCT Localizer Radiographs, 8th International Workshop on Bone Densitometry, Bad Reichenhall, Germany, Apr. 28–May 2, 1991. However, it is believed that the proposed CT images were not dual energy images and that the proposal may not completely address the issues of geometric distortions and/or vertebral magnification factor differences as between the AP and lateral images. Moreover, it is believed that QCT (quantitative computerized tomography) so used in morphometry typically images a relatively limited region of the spine such as the T12 through L4 vertebrae.

When bone densitometry equipment is used to obtain penetrating radiation images useful in morphometry, typically a patient is placed on a table and remains stationary while a radiation source moves relative to the patient position. A radiation detector is positioned on the opposite side of the table from the source to detect radiation transmitted through the patient. The radiation source and detector are usually mechanically linked by a structure such as a C-arm to ensure alignment between them. Both x-ray tubes and isotopes have been used as a source of the radiation. In each case, the radiation from the source is collimated to a specific beam shape prior to reaching the patient to thereby restrict the radiation field to the predetermined region of the patient opposite which are located the detectors. In the case of using x-rays, various beam shapes have been used in practice or proposed, including fan beam, pencil beam and cone or pyramid beam shapes.

Bone densitometry systems are manufactured by the assignee hereof under tradenames including QDR 2000plus, QDR-2000, QDR-1500, QDR-1000plus, QDR-1000W and QDR-1000. Certain information respecting such equipment can be found in brochures originating with the assignee hereof and identified by the designators B-108 (9/93) USA, B-109 (9/93) USA, S-117 (9/93) USA and S-118 (10/93) USA. Commonly owned U.S. patents pertaining to such systems include U.S. Pat. Nos. 4,811,373, 4,947,414, 4,953,189, 5,040,199, 5,044,002; 5,054,048, 5,067,144, 5,070,519, 5,132,995 and 5,148,455 as well as 4,986,273 and 5,165,410 (assigned on its face to Medical & Scientific Enterprises, Inc. but now commonly owned). Commonly owned U.S. patent application Ser. No. 08/156,287 filed on Nov. 22, 1993 also pertains to a bone densitometer. Said patents and application and said brochures are hereby incorporated by reference herein. Other bone densitometry systems are believed to be offered by other companies, such as the Lunar Corporation of Madison, Wis. See, e.g., J. Hanson, et al., New Imaging Bone Densitometer, Presented at: The American Society for Bone and Mineral Research 15th Annual Meeting, 18–22 Sep., 1993, Tampa, Fla., USA, an undated flier entitled Product Information EXPERT, and U.S. Pat. No. 5,228,068, none of which is necessarily admitted to be prior art against the invention claimed in herein. Note the discussion of an approach to morphometry in said U.S. Pat. No. 5,228,068.

For a general background concerning MXA, see Morphometric X-Ray Absorptiometry (MXA), a document prepared by the assignee hereof and identified by the designation W-126 (10/93) USA, which is hereby incorporated by reference.

SUMMARY OF THE INVENTION

A vertebral morphometry process in accordance with a nonlimiting example of the invention estimates vertebral body dimensional parameters to quantify vertebral deformities. For a morphometry examination in accordance with the invention, typically two scans are performed such as an AP centerline scan to determine spine alignment and a lateral morphometry scan for morphometric analysis. The centerline scan is an AP scan similar to that acquired in AP/Lateral scanning; however, whereas a typical centerline scan used for bone densitometry purposes may image a spinal region that is about 6 inches long, a typical centerline AP scan for morphometry in accordance with the invention can image a spinal region which in the range of 20 inches long. Similarly, the second morphometry scan, e.g., a lateral scan which images a spinal region which also can be in the range of about 20 inches in length. Both scans can include all thoracic and lumbar vertebrae, or a subset thereof such as thoracic vertebrae T4–T12 and lumbar vertebrae L1–L4.

Morphometry scans are analyzed in accordance with an example of the invention by defining the positions of three reference points, anterior, posterior, and mid, on each of the two endplates, superior and inferior, of each vertebral body. For a baseline morphometry scan, the centerline and morphometry scans are displayed side-by-side. The system can suggest point placements based upon its pre-stored knowledge of normal vertebral anatomy. Each vertebral body is described by its own coordinate system determined by the inferior anterior point of each vertebra and by a high-degree polynomial, such as a fourth degree polynomial, made to fit through those points. This is designed to reduce operator-induced variation and to accelerate image evaluation. An operator can change the suggested point positions by adjusting the positions on each displayed vertebral body of three markers on each endplate in ascending order. A second position cursor automatically tracks the position of the active reference point on the AP centerline scan. For each vertebral body analyzed, a Vertebral Dimensions Report can be created to provide estimates for: (a) posterior height, which is the distance between the posterior points on the superior and inferior endplates of the specific vertebral body; (b) mid height, which is the distance between the mid points on the superior and inferior endplates of the specific vertebral body; (c) anterior height, which is the distance between the anterior points on the superior and inferior endplates of that specific vertebral body; (d) wedge parameter, which is the ratio of the anterior height to the posterior height of that specific vertebral body; and (e) mwedge parameter, which is the ratio of the mid height to the posterior height of that specific vertebral body. In addition, during analysis of a follow-up morphometric scan using a "compare" feature, the follow-up morphometry scan can be displayed beside the baseline morphometry scan image. The vertebral endplate markers from the baseline scan analysis can transfer automatically onto the follow-up scan and move as a group to help position the markers as a group on the morphometry scan. Then, individual markers can be adjusted if necessary.

In broader terms, the invention is embodied in a method and a system which image a patient with dual energy penetrating radiation to obtain paired vertebral AP and lateral scan images and utilize the paired images to carry out computer-assisted vertebral morphometric analysis. In the course of the lateral scan, a constant vertebral magnification factor is maintained despite the fact that the vertebral centerline projection on a horizontal plane may curve or skew. In addition, the same vertebral magnification factor can be maintained for each of the AP and lateral scans. Still in addition, the same magnification factor can be maintained as between an initial examination and a later, follow up examination of the same patient. Stated differently, in accordance with one aspect of the invention a constant vertebral magnification factor can be maintained for all examinations of all patients, as well as within each examination, in order to ensure better fit of examination results to each other and to a knowledge database. Such constant vertebral magnification factor can be achieved by maintaining a constant distance between the source of the penetrating radiation and a vertebral centerline. The AP scan can be taken within a relatively short time interval, such as less than a minute (e.g., 25 seconds) while the lateral scan can take much longer, such as more than a minute (e.g., 10 minutes). If the AP scan will be used for bone mineral density analysis in addition to its use for morphometry in accordance with the invention, the AP scan also can take several minutes, e.g., 6 minutes. For the lateral scan, the fan beam of penetrating radiation can maintain an orientation in which one of the boundaries of the fan is substantially horizontal (and parallel to the patient bed surface). In addition to the parameters referred to above, the morphometry according to the invention can derive estimates of Kyphosis, Lordosis and Scoliosis parameters.

BRIEF DESCRIPTION OF THE DRAWINGS

A more complete understanding of the invention may be obtained from the following description when taken in conjunction with the drawings, in which.

DESCRIPTION OF A PREFERRED EMBODIMENT

Figure 1A:
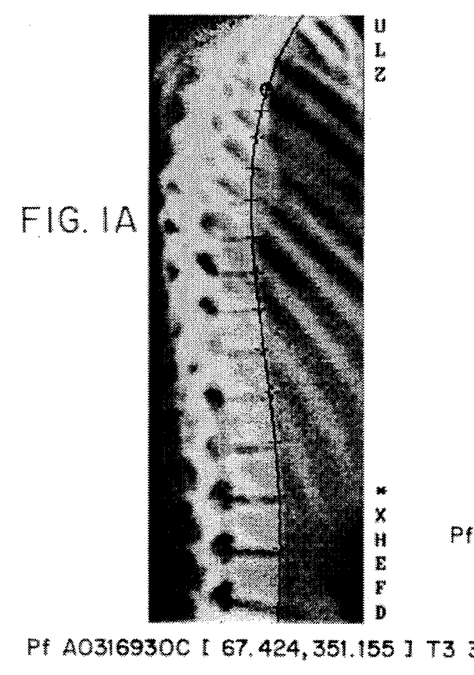
FIG. 1A and FIG. 1B illustrate a side-by-side display of paired lateral and AP vertebral images obtained and displayed in accordance with an embodiment of the invention for use in computer-assisted vertebral morphometry in accordance with the invention.
Figure 1B:
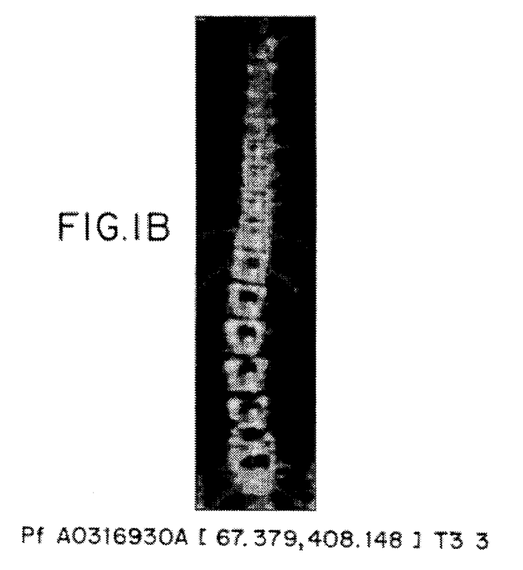

FIG. 1A and FIG. 1B illustrate a side-by-side display of a spinal lateral image on the left and a spinal AP image on the right, respectively obtained with the previously identified QDR-2000 series bone densitometry system available from the common assignee. For morphometry purposes, the operation of the commercially available system is modified under the control of morphometry software operating in accordance with the invention, in conjunction with the commercially available control software for the systems installed in this country, which is hereby incorporated by reference. The morphometry software is provided as a microfiche appendix.

Figure 3A:
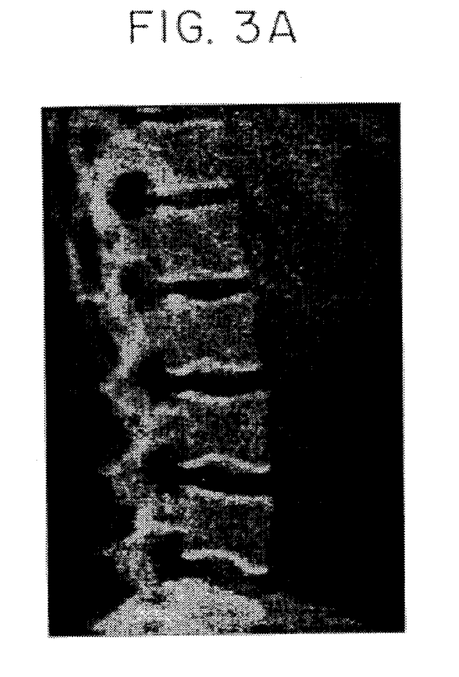
FIG. 3A amd FIG. 3B illustrate a display of an enlarged lateral image and a corresponding AP image, respectively.
Figure 3B:
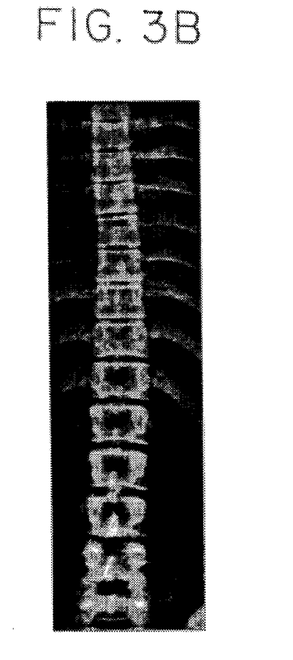
Figure 4:
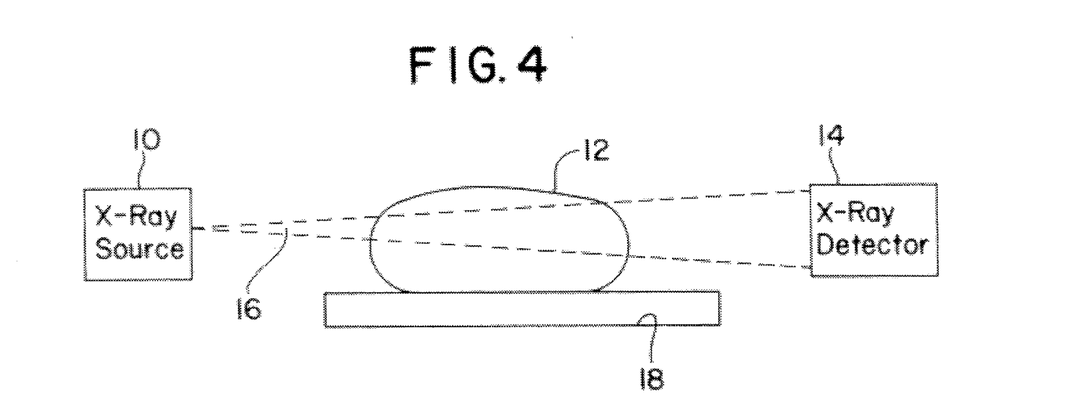
FIG. 4 illustrates the orientation of a fan beam of x-rays for a lateral scan.
Figure 5:
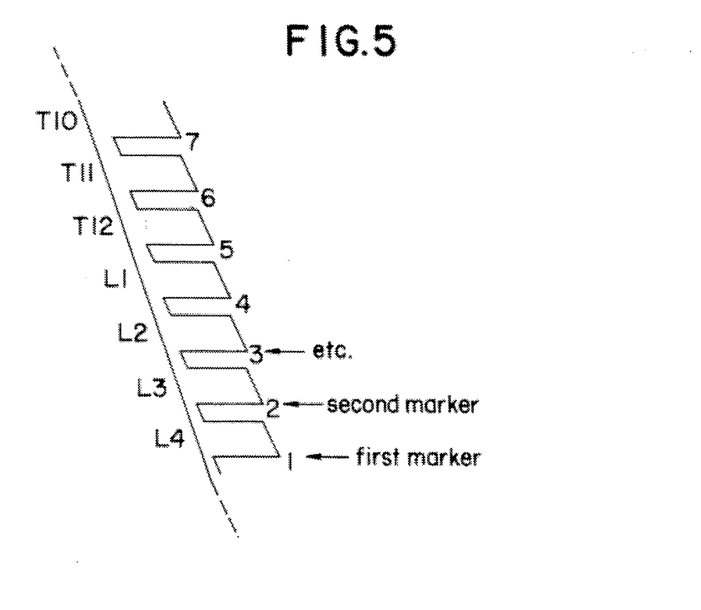
FIG. 5 illustrates a procedure for placing markers on a lateral vertebral image.
Figure 6A:
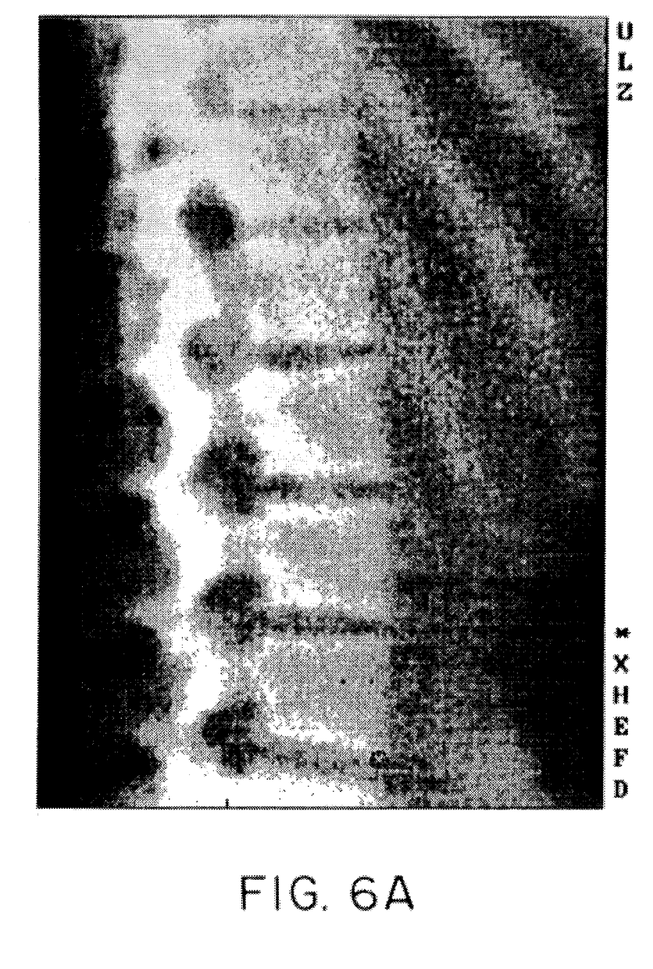
FIG. 6A and FIG. 6B illustrate an enlarged lateral image and an AP image, respectively with corresponding synchronized markers or cursors thereon.
Figure 6B:
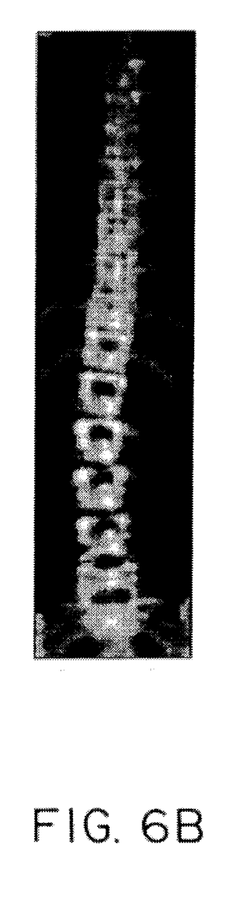
Figure 7:
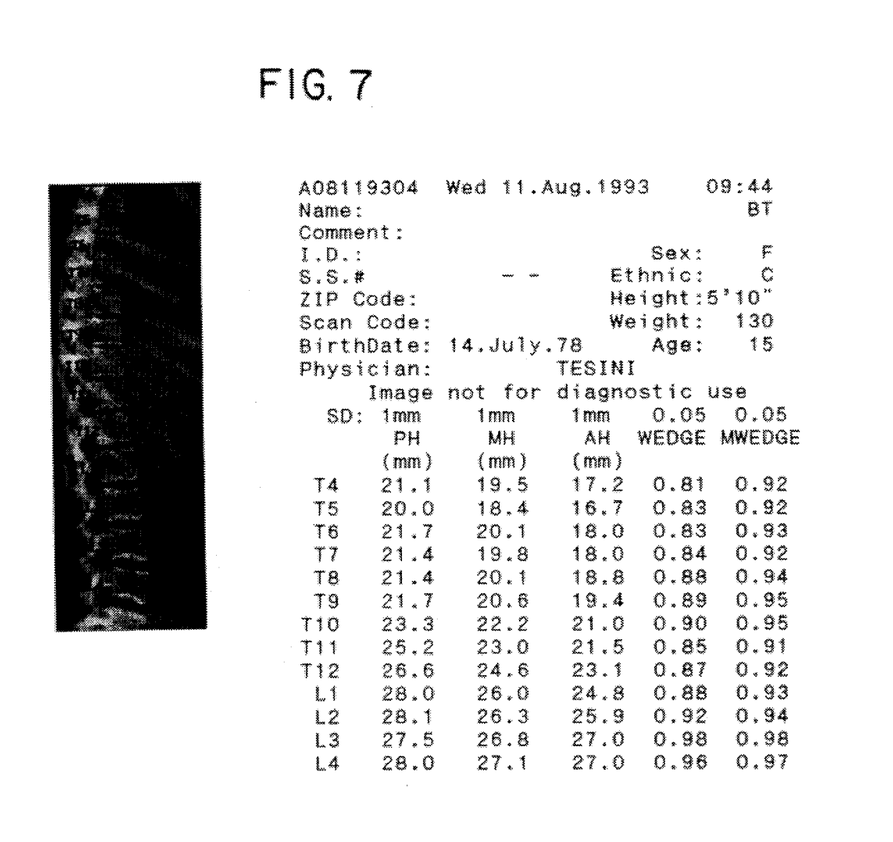
FIG. 7 illustrates a vertebral dimensions report.
Figure 8:
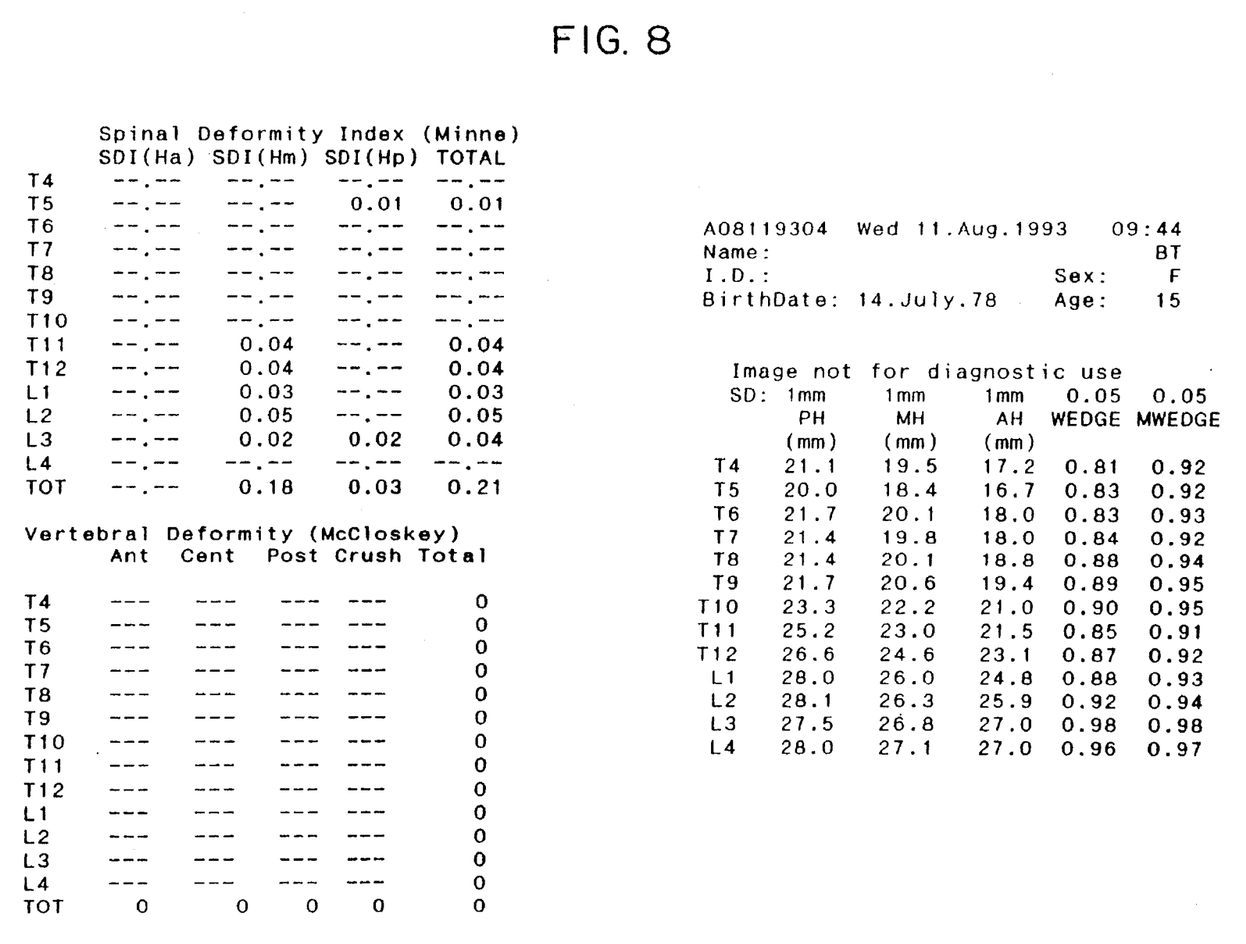
FIG. 8 illustrates morphometry summary analysis report.
Figure 9:
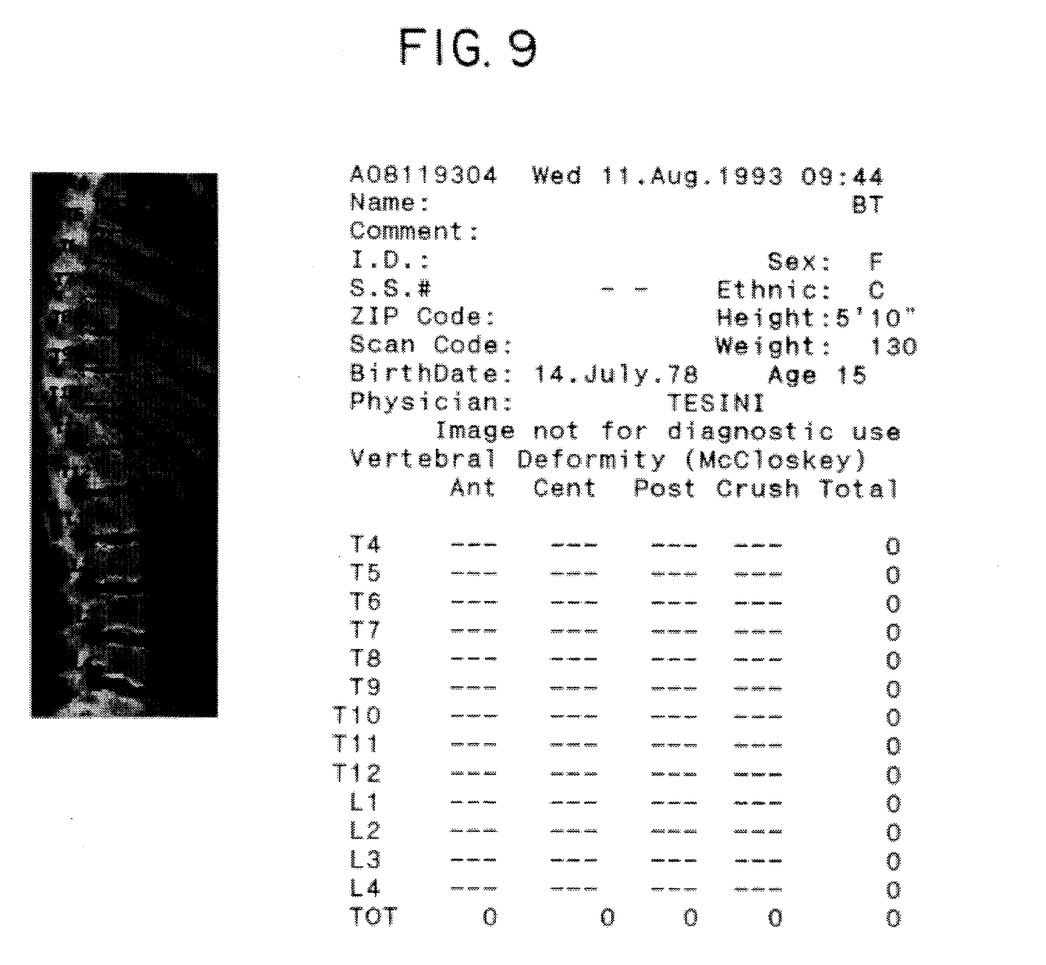
FIG. 9 illustrates a vertebral deformity report.
Figure 10:
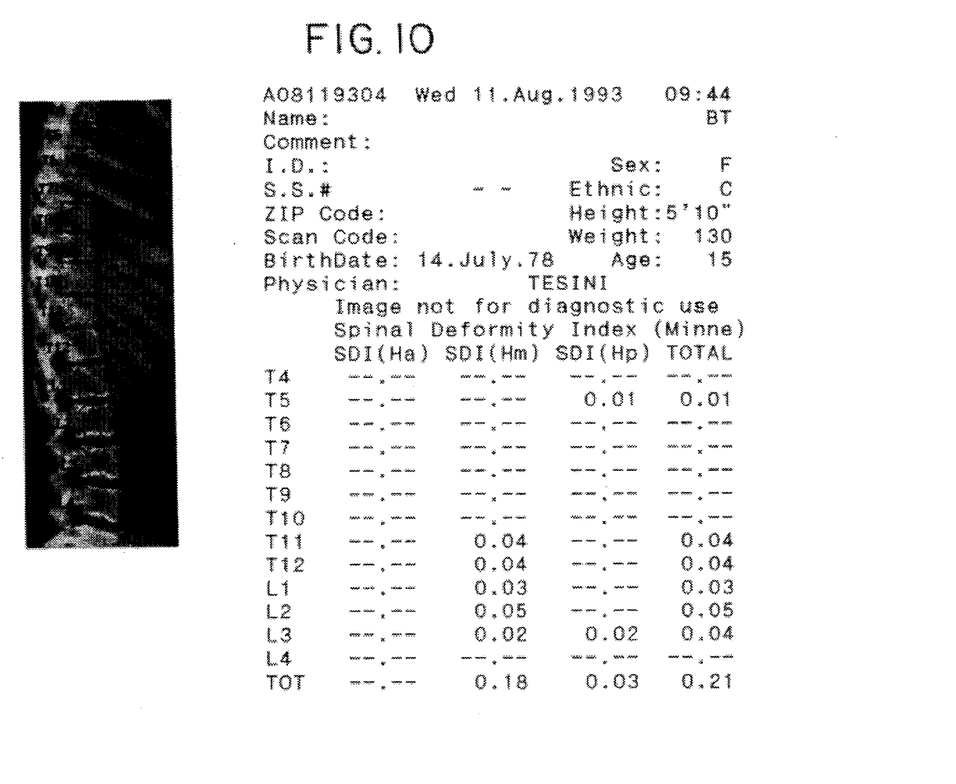
FIG. 10 illustrates a spinal deformity report.
Figure 11A:
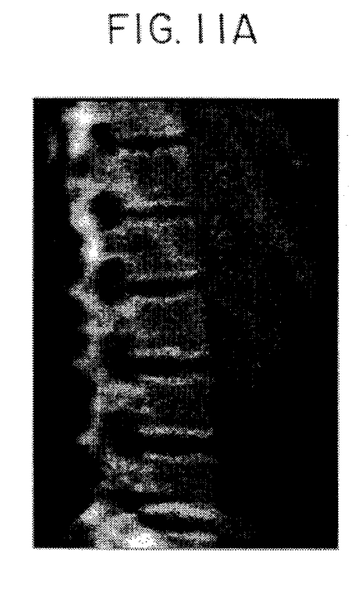
FIG. 11A and FIG. 11B illustrate analysis of a follow-up morphometry scan.
Figure 11B:
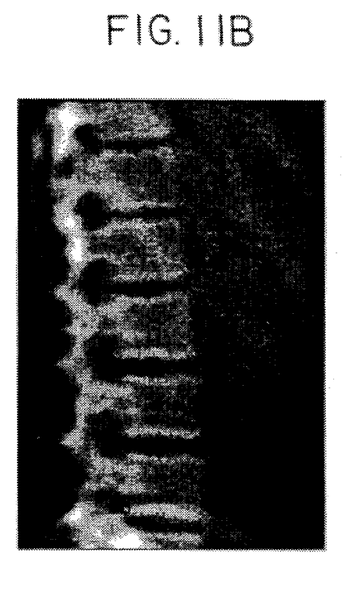

To obtain paired AP and lateral images of the type illustrated in FIG. 1A and FIG. 1B, the bone densitometry system first carries out an AP scan, modified in accordance with the invention to cover a longer region of the spine, to obtain the AP image shown in FIG. 1B. This image is obtained by scanning a supine patient, for example a patient in the position illustrated in FIG. 2, with a fan beam of x-rays oriented such that the central axis of the x-ray beam is vertical. A procedure for obtaining the paired scans and processing them is described in pages G1–34 of the QDR-2000 Operator's Manual and User's Guide supplied by Hologic, Inc. of Waltham, Mass., Document No. 080-0384 Revision E, which pages are hereby incorporated by reference. In the example illustrated in FIG. 2, the x-ray source is below the patient and the x-ray detectors are above the patient, and the patient is centered on a table such that the vertebral column centerline substantially coincides with the central axis of the fan beam. The resulting image is still called an AP (anterior-posterior) image in this specification, although in this configuration it can be called more accurately a PA (posterior-anterior) image. For the purposes of this invention, no distinction is made between AP and PA images. Unless the AP image is to be used for other purposes, such as for bone mineral density analysis, it can be taken relatively quickly, such as over a time of less than a minute (e.g., 25 seconds). The image resolution therefore can be lower, but sufficient for morphometry purposes in accordance with the invention, and the overall examination time and patient dose can be thus reduced. The system generates the AP image and carries out image processing which includes an identification of a vertebral centerline and a start position and a region of interest for the morphometry scan. A C-arm which supports the x-ray source and detector is then pivoted while the patient remains in the supine position such that, as illustrated in FIG. 4, x-ray source 10 is at one side of patient 12 while x-ray detector 14 is at the other side, and such that one boundary of fan-shaped x-ray beam 16 is horizontal and parallel to the top surface of patient table 18. The line connecting the lowermost detector element in x-ray detector 14 and the origin of beam 16 is just above table 18, e.g., ⅛" to ¼" above the table. In this manner, geometric distortion can be suppressed and the measured x-ray beam need not pass through table 18. The system then carries out a lateral scan in which the distance between the origin of beam 16 and the vertebral centerline is the same as for the AP scan and, moreover, remains the same during the lateral scan even if the projection of the centerline on a horizontal plane deviates (within limits) from a straight line or from a line perpendicular to the plane defined by the origin of beam 16 and detector elements in x-ray detector 14. To maintain the distance between the beam origin and the vertebral centerline constant, the source-detector assembly can move along the source-detector axis during the lateral scan, as controlled by the software controlling the morphometry scan in accordance with the invention, depending on the position of the vertebral centerline identified as a result of the AP scan. After the lateral scan image is available, and is displayed alongside the AP image as illustrated in FIG. 1A and FIG. 1B, markers are placed on the endplates of each vertebral body, for example in the spinal region including vertebrae T4–L4, on three reference points (anterior, posterior, and mid) on each of the two endplates (inferior and superior) of each vertebrae. The preferred procedure for placing markers is: placement of Inferior Anterior Points; adjustment of Inferior Posterior Points; adjustment of Superior Anterior Point for L4; adjustment of Point Positions Relative to Fit; and adjustment of Point Positions Relative to Image. At each phase in this procedure, the system suggests point placements based upon its knowledge of normal vertebral anatomy. Each vertebral body is described by its own coordinate system determined by the inferior anterior point of each vertebra, and a fourth degree polynomial fit through those points is made. This is designed to reduce operator-induced variation and to accelerate image evaluation. A dual windowing feature in the system allows the operator to scroll the image (the lateral image) in FIG. 1A up or down while the image (the AP image) in FIG. 1B remains fixed and shows the entire spinal region which was imaged in the AP scan. Such scrolling is illustrated in FIG. 3A and FIG. 3B. If while placing markers the operator moves a marker off the screen (up or down), the system can automatically scroll the display to show that portion of the spine. In a preferred embodiment of the invention, an active marker is displayed as a blue circle on the image in FIG. 1A. The position, on the spine, of the active marker is denoted on the image in FIG. 1B by a blue dashed line which moves along the AP image in synchronism with any movement of the marker on the image in FIG. 1A, in order to ensure that the markers on the two images shown in FIG. 1A and FIG. 1B, respectively, track each other in position at all times. Markers are placed sequentially, as indicated in FIG. 5, beginning with the anterior marker on the inferior endplate of the lowest vertebra of interest, in this case L4. The operator observes the markings which are already placed on the image (lateral) in FIG. 1A by the system derived from on a knowledge database of typical vertebral anatomy. The operator moves the first marker, using arrow keys or a mouse that can be provided as a part of a commercial QDR-2000 system, so that the marker is located as close to the inferior endplate, and as far to the anterior, as possible without going outside of the vertebral body. After the first marker is positioned correctly, the operator presses an <Insert> key, in response to which the system stores information defining the position and identity of the point. The system automatically changes the active marker to the next vertebral body, which the operator similarly positions and enters. The system and the operator continue up the spine until all markers for anterior point positions, on the inferior endplate, are complete. The system provides the location of the active point (vertebral body level) and the active marker number. This is displayed under the morphometry image at the far right as illustrated in FIG. 1A and FIG. 1B. The first two characters provide the location on the spine (specific vertebral body), and the last number indicates the active marker. A similar procedure adjusts the inferior posterior point positions. Points are adjusted beginning with the posterior marker on the inferior endplate of L4 in this example. Similarly, the superior anterior point positions are adjusted. A group of points can be moved with respect to the curve of the spine. When the points are positioned correctly, a report can be generated. Morphometry scan results can be reported by different methods illustrated in FIGS. 7, 8, 9 and 10. A Vertebral Dimensions Report (FIG. 7) shows the vertebral dimensions in millimeters (mm). Anterior (AH), mid- (MH) and posterior (PH) vertebral heights are listed. Anterior/posterior height ratios (WEDGE) and mid/posterior (MWEDGE) height ratios are also provided. A Morphometry Summary Analysis Report (FIG. 8) shows the calculations (only) from each of the other report screens. Since all of the calculations appear on one page, this report can provide a convenient presentation of the information. A Vertebral Deformity Report (FIG. 9) labels vertebral deformities according to an algorithm proposed, e.g., by McCloskey et al. (McCloskey E. V., Spector T. D., Eyres K. S., O'Rourke N., Fern D. E., Kanis J. A. 1993 Assessment of vertebral deformity—validation of a new method with high specificity. Osteoporosis Int 3(3): 138–147). Anterior, central, posterior and crush deformities are evaluated separately. The number of deformities is totaled per vertebra and per deformity type. A Spinal Deformity Index Report shows the Spine Deformity Index (SDI) as proposed, e.g., by Minne et al. (Minne H. W., Leidig G., Wuster C. H. R., et al., 1988 A newly developed spine deformity index (SDI) to quantify vertebral crush fractures in patients with osteoporosis. Bone Mineral 3: 335–349). A number greater than 0 indicates a deformity, while a no entry indicates that a vertebra is not considered significantly deformed. Indices are listed separately for anterior (Ha), mid (Hm) and posterior (Hp) vertebral heights. The indices are totaled per vertebra and per deformity type. In accordance with another feature of the invention, a Compare procedure can be used on follow-up scans to optimize marker placements from one scan to another, and to save time. Since marker positions, on a new scan of the same patient, are likely to be very close to the prior scan, time can be saved by automatically matching-up the markers in accordance with the invention. The Compare procedure comprises: Scan selection; Image adjustment; Marker placement; and Report generation. The Scan Selection step is the selection of a baseline scan for the comparison. The Image Adjustment step comprises adjusting the contrast and brightness of the displayed image, if necessary, to give the best definition to the vertebral endplates. In the Marker Placement step, the current (follow-up) morphometry scan appears on the left of the screen as illlustrated in FIG. 11A and the baseline scan appears on the right, as illustrated in FIG. 11B. The system transfers the marker positions from the baseline to the follow-up morphometry scan. The operator can adjust the points on the image (the lateral image) in FIG. 11A as a group to allow compensation for changes in spinal curvature that may have occurred between the two scans due to positioning changes or due to changes in patient anatomy. If the shape of the vertebral bodies has changed, it may be easier to reposition markers using the "Adjust Positions Relative to Image" capability of the system after having used the "Adjust Positions Relative to Fit" capability.

Stated in more formal terms, MXA Scan analysis in accordance with an exemplary embodiment of the invention can be viewed as a process of placing points on the lateral morphometry image at the anterior, mid, and posterior positions of the inferior and superior endpoints for each vertebral body in the spinal region of interest. These point locations are then used to calculate the anterior, mid, and posterior heights of the vertebral bodies. These heights are then compared to one another and to known normal values for the heights and ratios of the heights for each vertebral body and among vertebral bodies to quantify the degree of vertebral deformity.

MXA Scan analysis in accordance with the invention can follow an algorithm which is a knowledge based and semi-automatic procedure for placing the required points. For baseline scans (no previous analyzed scan for the patient), the algorithm can use prior knowledge of relationships between vertebral heights based on published literature and on analysis of morphometric measurements previously carried out in accordance with the invention for other patients and selected in accordance with objective and/or subjective criteria for inclusion in the knowledge database. As information is supplied for a given patient, the algorithm incorporates that information to adjust the proposed placement of the points. For FollowUp scans, the previous scan results are used as the initial guess for the placement of points and modified to compensate for changes in patient positioning and/or possible deformity of the vertebral bodies. Points are placed either by moving a cursor via directional commands entered on the computer keyboard or by manipulation of the positions via a pointing device such as a mouse. The algorithm is substantially the same regardless of which implementation is used, except as noted below.

The following steps are followed for Baseline Scans in accordance with a non-limiting example of the invention. Note that an example of the software controlling the process is set forth in the microfiche appendix:

1. An operator of the system places (preferably with a mouse) one point per vertebra starting at L4 and extending 1 vertebra beyond the topmost vertebra to be quantified. The points should follow the outline of anterior edges and should be placed at the inferior anterior edge of the endplates. This generates a set of I anterior points $A_1$–$A_I$, where $A_i$ is defined by coordinates $(X_{ai}, Y_{ai})$. If the mouse is not being used, then the algorithm guesses at the point position for the next vertebra based on the position(s) of the points on the inferior vertebrae.

2. A 4th degree polynomial is fit through $A_1$–$A_I$:

$$x = a_a y + b_a y^2 + c_a y^3 + d_a y^4 + e_a \tag{1}$$

Note that x (posterior/anterior axis) is fit as a function of y (caudal to cranial axis).

Figures 1C, 2:
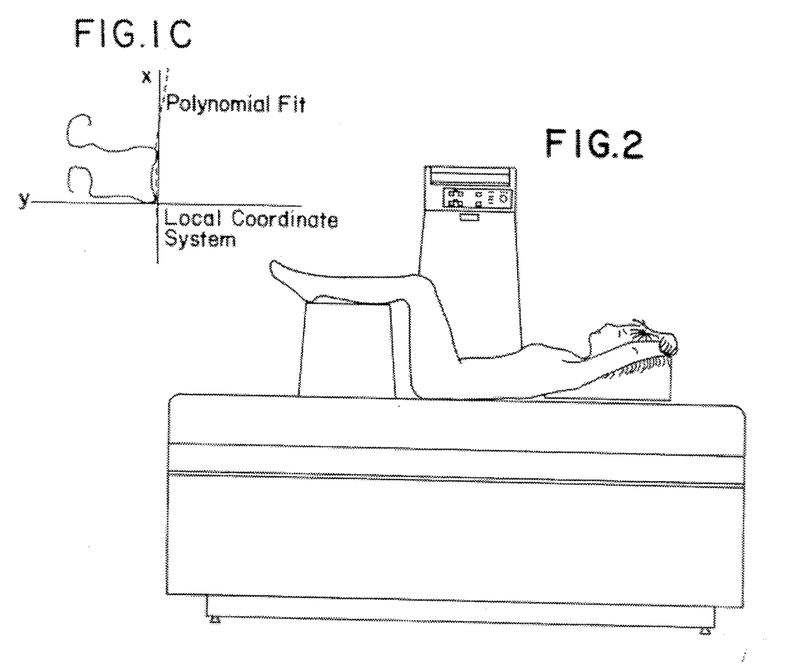
FIG. 1C illustrates a local coordinate system used for each vertebra in accordance with an embodiment of the invention.
FIG. 2 illustrates a patient positioned for centerline AP/morphometry scans.

3. For each vertebral body, a local coordinate system is defined with the inferior anterior point of the vertebral body as the origin and the perpendicular to the fit as the local y axis, as illustrated in FIG. 1C:

4. The process generates a set of inferior posterior points for the specified vertebral bodies. The points are initially positioned relative to the respective local coordinate system for each vertebral body at a distance from the inferior anterior point proportional to the distance between the inferior posterior point and inferior anterior point on the lowest vertebral body. The ratio of these distances can be maintained in the knowledge base which guides the process. The operator then adjusts the positions of the inferior posterior points for the respective vertebrae. As a point is adjusted, similar adjustments are made automatically to inferior posterior points on superior vertebral bodies preserving the angle between local y axis and a line connecting the inferior posterior and anterior points and the ratio of the distances between the inferior posterior and anterior points.

5. The process generates a single superior posterior point at a predefined distance along the 4th order fit. The operator then adjusts the location of this point.

6. The process then generates the remaining points as follows:

a) Superior anterior points are generated along the fit at distances proportional to the distance between the inferior anterior and superior anterior points on the lowest vertebral body. The ratio of these distances is maintained in the knowledge base which guides the process.

b) Superior posterior points are generated similarly as if the anterior fit passed through the inferior posterior point. For the lowest vertebra (usually but not necessarily L4), the posterior height is calculated as a fixed proportion of the anterior height. For the remaining vertebrae, superior posterior points are then generated at distances proportional to the distance between the inferior posterior and superior posterior points on the lowest vertebral body. The ratios of these distances are maintained in the knowledge base which guides the process.

c) Superior and Inferior midpoints are then generated. A point (l) is calculated midway between the inferior posterior and anterior points. A second point (u) is calculated midway between the superior posterior and anterior points. The inferior and superior midpoints are then located along a line connecting l and u such that the distance between the inferior and superior midpoints corresponds to data in the knowledge base. The inferior and superior midpoints are offset equally from the points (l) and (u).

7. The operator then adjusts the points as described below. Point positions are stored at grid locations where the grid spacing is a function of the data acquisition. All distances are expressed in millimeters.

To adjust point positions after the points are placed as discussed above, the process supplies three (3) modes of adjustment:

1) Selected points (relative to fit). The subset of points which can be moved is a function of the currently selected cursor. Point motion is performed relative to the fourth order polynomial fit in the local coordinate system of each vertebral body as defined above. The possible motions are summarized below for the different candidate cursor positions:

a) Cursor at inferior anterior point. The fit is recalculated as the inferior anterior point is moved. The positions of all points on all vertebrae relative to their local coordinate system are preserved.

b) Cursor at inferior posterior point. The angle and distance of the inferior mid and superior anterior points are adjusted corresponding to changes in the angle and distance of the inferior posterior point relative to a coordinate system centered at the inferior anterior point. The angle and distance of the superior posterior and superior mid points are adjusted relative by a similar amount by relative to the new position of the superior anterior point (e.g., if the angle of the inferior posterior point changes 10 degrees relative to the inferior anterior point, then the angle of the superior posterior point changes 10 degrees relative to the angle between the old superior posterior and superior anterior points but calculated from the new superior anterior point position).

c) Cursor at inferior mid point. The superior mid point is adjusted relative to the current superior anterior point proportional to the change in the position of the inferior midpoint relative to the inferior anterior point.

d) Cursor at superior posterior point. The superior mid point is adjusted relative to the current superior anterior point proportional to the change in the position of the superior posterior point relative to the superior anterior point e) Cursor at superior anterior point. The superior mid and superior posterior points are adjusted relative to the inferior anterior point proportional to the change in the position of the superior anterior point relative to the inferior anterior point.

f) Cursor at superior mid point. Only the superior mid point is moved. In each case, point positions in vertebral bodies superior to the current vertebral body are also adjusted. Motion is limited so that no point can be moved outside the image frame.

2) Individual point. Only the specified point is moved. The point to be moved is indicated by color and a cursor. The point position may be changed via the keyboard or the mouse.

3) All points (relative to image). All the points may be moved. All the points are marked in a color to indicate that they are moveable. A specific point is indicated as a cursor although all the points move as a group. Point positions may be changed via the keyboard or the mouse. Motion is the same for all points. Motion is limited such that no point can be moved outside the image frame.

In baseline scans, the operator first performs type 1 adjustments and then proceeds to move individual points, if necessary, using type 2 adjustments. Type 3 adjustments are intended for Follow-Up scans to compensate for overall shifts in general position positioning.

In the case of follow-up scans, where morphometry in accordance with the invention has been carried out for the patient on a previous occasion to obtain a Baseline Scan, a Follow-Up Scan procedure is followed:

1. Baseline and follow-up scans are presented side-by-side. The point positions from the previous (baseline) scan are reproduced on the follow-up scan. The operator initially performs a type 3 repositioning (all points relative to image) to compensate for any overall shift in patient positioning (or initial scan starting position)

2. The operator then selects type 1 repositioning (relative to fit) and adjusts the point positions to reflect differences in the curvature of the spine. For the most part, the operator will need to select and adjust specific inferior anterior positions to reproduce the coordinate system for each vertebral body. In the case of incident deformity, the operator should also adjust the endplates by moving the inferior and superior posterior point positions and possibly even correct the mid point placement (if necessary).

3. If necessary, the operator can reposition individual points using type 1 repositioning.

Figure 16:
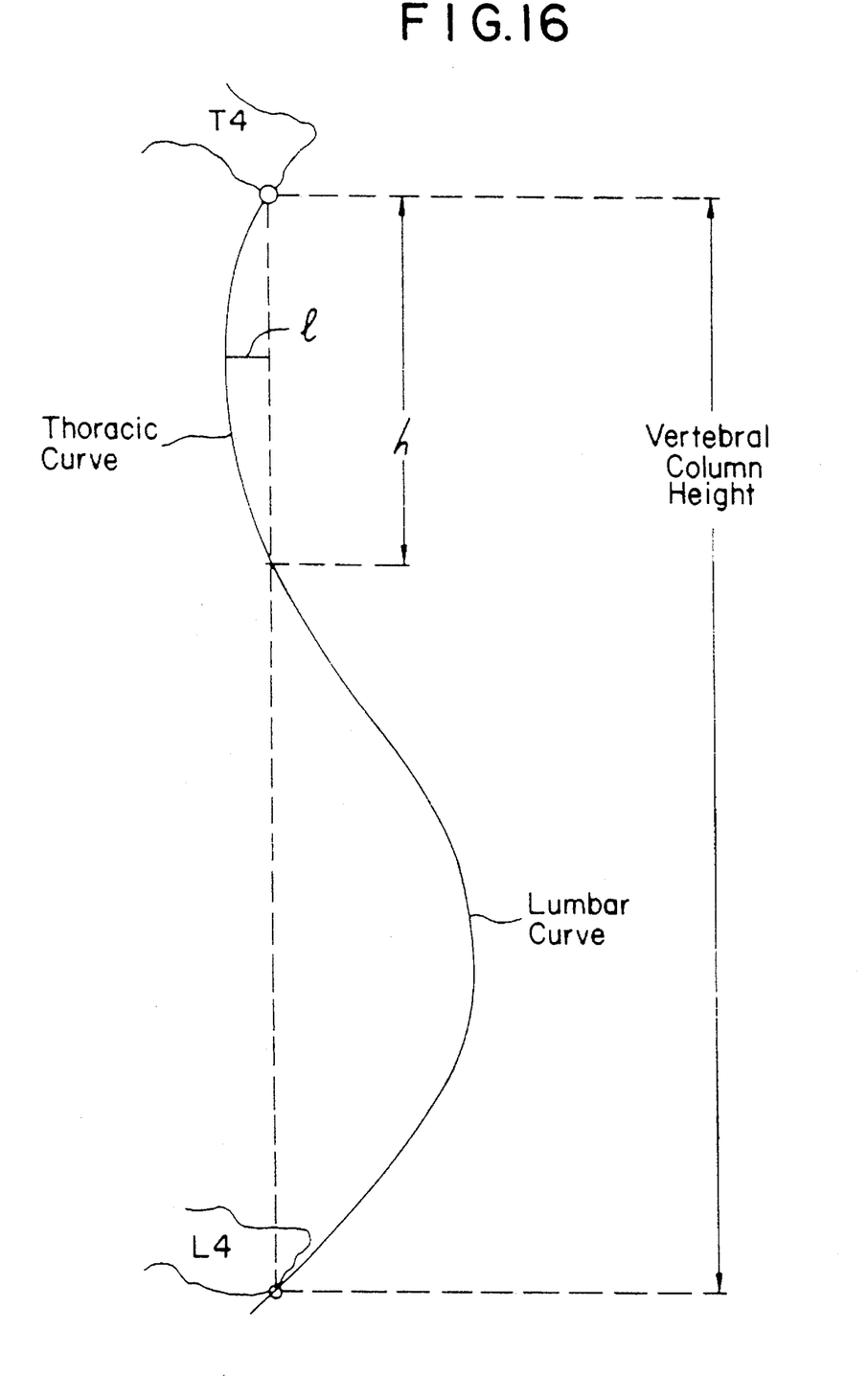
FIG. 16 ilustrates the measurement of a Kyphosis factor.

The results of the procedures described above can be used to calculate and assess a number of additional parameters characterizing a patient. For example, a Kyphosis index can be calculated in accordance with the invention as illustrated in FIG. 16, by measuring the distance (l) between the lower anterior point on T4 and the intersection of the spinal centerline with a straight line from that point on T4 and the corresponding point on L4, measuring the distance (h) from that line to the thoracic curve, and multiplying the ratio (h/l) by the factor 100.

Figure 12:
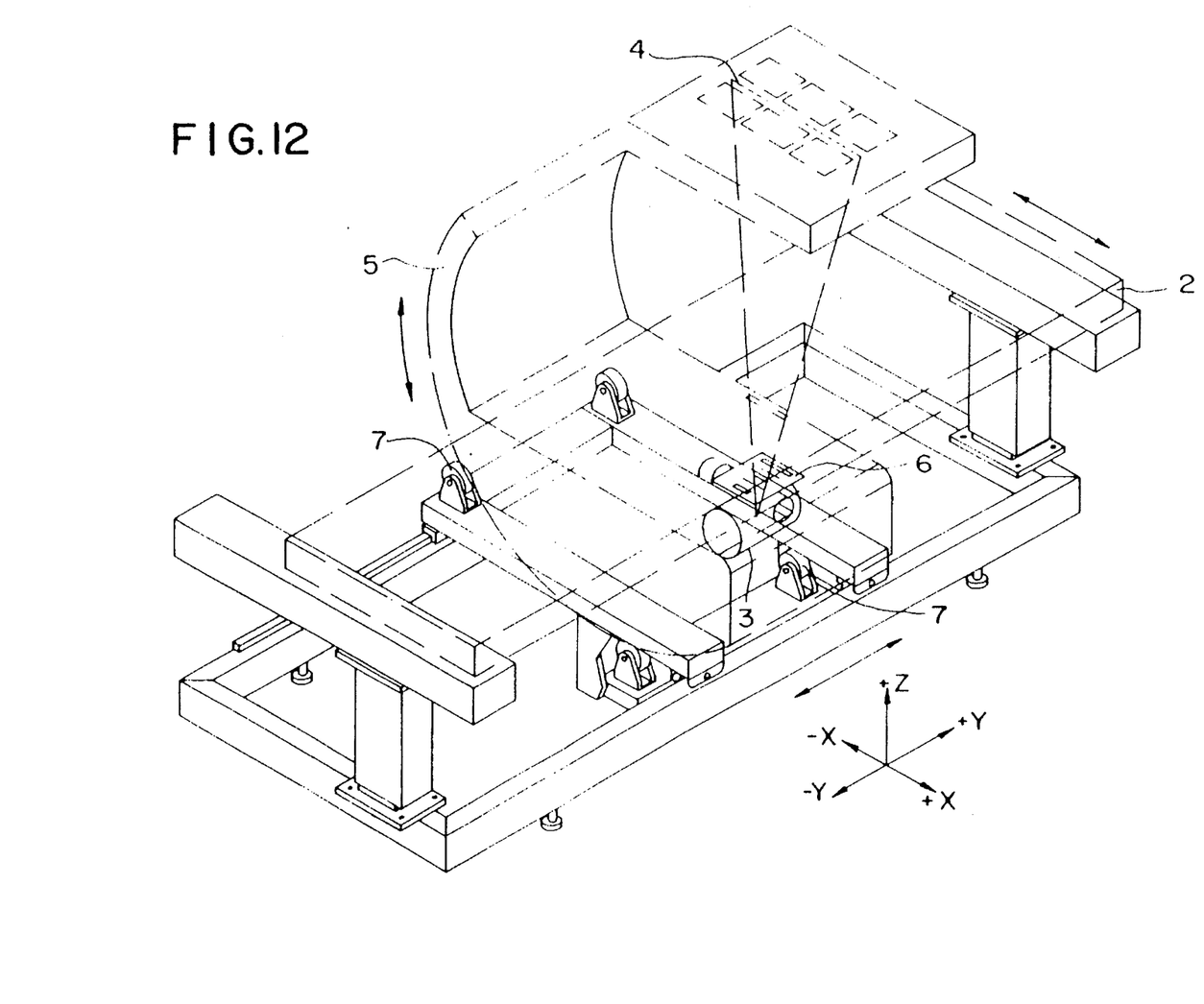
FIG. 12 is a perspective view illustrating an alternative bone densitometry system useful in practicing the invention.
Figure 13:
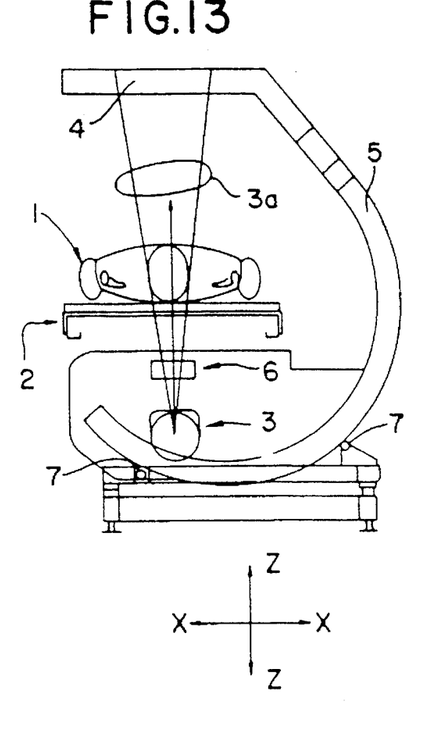
FIG. 13 is a sectional view illustrating the system of FIG. 12 when used for an AP scan.
Figure 14:
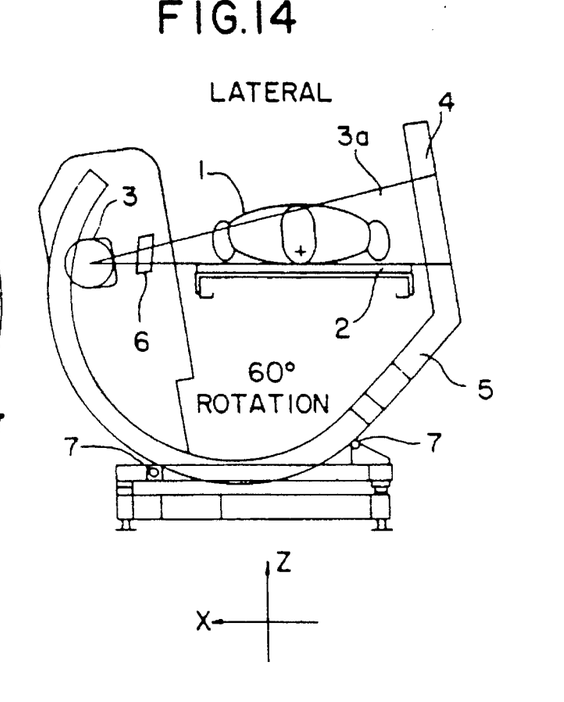
FIG. 14 is a sectional view similar to that of FIG. 13 but illustrating the system when used for a lateral scan.

While the description above refers to using a QDR-2000 system to obtain the AP and lateral images, in the alternative the system described in said commonly owned patent application and illustrated in FIGS. 12, 13 and 14 can be used. As illustrated in FIGS. 12–14, a patient 1 lies horizontally (in a supine position) during scanning on a table 2. X-ray radiation produced by an x-ray source 3 located beneath table 2 is transmitted through patient 1 to a detector 4 having an array of detector positions and located above patient 1. Both x-ray source 3 and detector 4 are supported on a rigid arm 5 which maintains a selected source-to-detector distance and alignment. In this example of the invention, x-ray source 3 has a stationary anode. Adjacent x-ray source 3 is a slit collimator 6 made of a material an x-ray opaque material such as lead or tungsten of sufficient thickness to substantially block x-rays from source 3. One or more selectable slits have been machined into collimator 6 to allow passage of the x-rays therethrough. The preferred embodiment includes a 1 mm wide collimator slit. The x-ray radiation from the x-ray source 3 passes through the slit in the collimator 6 and forms a fan shaped beam of x-rays 3a. The angle subtended by beam 3a and the distance between its origin at the focal spot of the x-ray tube and patient 1 are selected such that beam 3a would not cover the entire cross-section of a typical adult patient at any one time but would cover only a selected portion of the width. In the preferred embodiment, fan beam 3a has a maximum fan angle of 22 degrees. Of course, x-ray beam 3a not only has width (along the X-axis illustrated in the Figures) but also has a thickness along the Y-axis that is defined by the width of the slit in collimator 6 and its distance from the origin of beam 3a. A scan line is defined by the area of the patient irradiated at any one time, i.e. the width and thickness of the x-ray beam over which data is collected at one point in time. A complete pass or scan consists of a set of adjacent scan lines obtained over a period of time such that the entire region of interest has been measured.

Opposite x-ray source 3 is detector 4 which in this embodiment comprises approximately 200 detector elements arranged in a linear configuration along the XZ plane which is about 16" long and is about 42" from the origin of beam 3a (42" source-to-detector spacing) and subtends a 22 degree fan angle. The detector elements making up detector 4 are fixed with respect to x-ray source 3. However, both x-ray source 3 and detector 4 can move with respect to patient 1 and table 2. One motion translates fan beam 3a along the patient axis defined by the spine, i.e., in the Y-direction. Another motion rotates beam 3a around the patient. The center of rotation is at a point C determined by the support arm 5 and the method of rotation employed. In this embodiment, the detectors and x-ray source are mounted to C-arm 5 which rotates on a set of rollers 7. Thus, the center of rotation is determined by the outer radius R of the C-arm, and is not at the origin (focal spot) of beam 3a.

Table 2 can move horizontally along the X-axis as well as vertically along the Z-axis. These motions can be carried out by using a toothed-belt driven by a stepping motor or a DC servo motor, although other implementations such as stepper-motor driven lead-screws can also be employed. To perform a scan, a series of scan lines of data must be acquired. To do this, C-arm 5 carrying the x-ray source 3 and detector 4 is moved along the Y-axis along the length of patient 1. This motion moves detector 4 and x-ray source 3 to form a succession of spatially overlapping scan lines adding up to a scanned rectangular area. The signals produced by the detectors in response to x-rays impinging thereon at successive scan lines are digitized by an analog to digital (A/D) converter and are stored, for example on disk. A computer processes the signals from the A/D converter into density representations and images using the principles disclosed in the prior art discussed in the background section of this disclosure.

For body structures of interest such as the spine, only a single pass of fan beam 3a along the Y-axis is required because typically the area of interest in the patient's body is covered by fan beam 3a as shown in FIGS. 13 and 14 for the Posteroanterior (PA) spine. However, in order to reduce geometric distortion and improve registration between lateral and PA views, in accordance with the invention the system maintains a substantially constant distance between x-ray source 3 and a centerline of the spine of patient 1. To achieve this, a series of movements of C-arm 5 and table 2 are required to ensure that the table and C-arm clear each other and to ensure that the requisite source-spine distance is maintained. In this embodiment, table 2 is moved along the X-axis and the Z-axis appropriately while C-arm 5 is rotated about an Y-axis passing through point C until the desired lateral position is reached.

Figure 15:
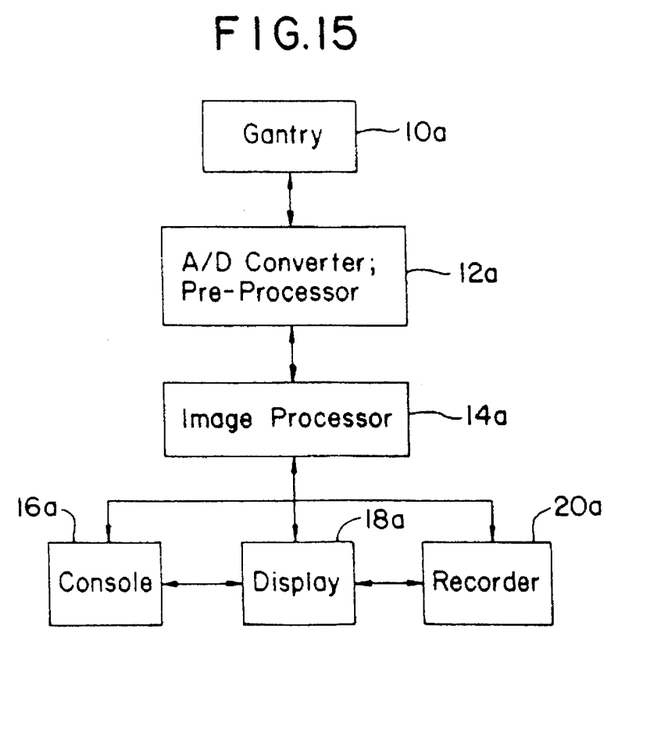
FIG. 15 is a block diagram illustrating functional components of a system useful in carrying out an embodiment of the invention.

FIG. 15 illustrates an embodiment in accordance with the invention in block diagram form. Gantry 10 includes the structure illustrated in FIGS. 12–14 as well as a suitable power supply for the x-ray tube and the motors needed to move table 2 and C-arm 5 and to operate collimator 6 in a manner similar to that in said QDR-2000 system. Detector 4 supplies x-ray measurements to A/D convertor and preliminary processor 12 which carries out processing similar to that carried out in said QDR-2000 system. The output of element 12 is supplied to a processor 14 which performs various calculations and forms an image in a manner similar to that used in said QDR-2000 system and, additionally, carries out morphometric calculations. Data and images from processor 14 are supplied to a console 16, display 18 and a recording device 20 for purposes and in a manner similar to those in said QDR-2000 system. Two-way arrows connect the elements of FIG. 15 to illustrate the fact that two-way communication can take place therebetween. Conventional elements have been omitted from the Figures and from this description for the sake of conciseness.

For example, the illustrated equipment can be used as a first step to derive a PA view of the patient's spine. The view can be in the form of a processed image in digital form, or it can be in the form of hard copy on x-ray film or on some other medium. The PA spine image is analyzed to determine the center of the vertebral column, and this information is used to maintain during a lateral scan the same distance between the source and the spine centerline as during the PA scan. For example, the each of the PA and lateral scans can cover entire T4 to L4 range in a single scan at a source to detector distance of 40 inches.

When both a PA view and a lateral view are available, selected points on the vertebrae images can be marked, for example as discussed in [5, 6]. For example, each vertebral body is outlined by six points which can serve as the basis of the calculation of posterior, mid- and anterior heights.

While a preferred embodiment of the invention has been described in detail, it should be understood that changes and variations will be apparent to those skilled in the art which are within the scope of the invention recited in the appended claims.

We claim:

1. A method comprising the steps of:

obtaining paired AP (anterior/posterior or posterior/anterior) centerline and lateral morphometry images of a patient covering at least the T4 (thoracic 4) through L4 (lumbar 4) vertebrae by using a fan beam bone densitometer to carry out an AP scan and a lateral scan without moving the patient between the scans, wherein said AP scan is carried out first to produce an AP image which is analyzed to determine the centerline of the patient's vertebral column and said centerline is used to maintain a constant distance between the centerline and an origin on the fan beam while carrying out the lateral scan;

displaying the paired AP image and the lateral image side-by-side together with a pair of spatially synchronized cursors pointing to anatomically corresponding current locations on both images to help identify vertebrae and visualize spatial relationships of anatomy and pathology between said AP and lateral images which are displayed side-by-side;

designating six points for each vertebra with said cursor;

calculating posterior, mid- and anterior vertebral heights and vertebral wedge indices with the use of points designated in the designating step; and displaying calculated heights and indices characterizing the patient.

2. A method as in claim 1 in which the step of obtaining said images comprises maintaining during said lateral scan an orientation of the fan beam in which one of the boundaries of the fan beam is horizontal.

3. A vertebral morphometry method comprising the steps of:
   imaging a patient with penetrating radiation to obtain paired vertebral AP (anterior/posterior or posterior/anterior) and lateral scan images;
   displaying said images side-by-side together with a pair of spatially synchronized cursors pointing to respective spatially corresponding points on said AP and lateral images to help identify vertebrae and visualize spatial relationships of anatomy and pathology between said AP and lateral images which are displayed side-by-side;
   utilizing the displayed images and said synchronized cursors to carry out computer-assisted vertebral morphometric analysis.

4. A method as in claim 3 in which the imaging step comprises maintaining a constant vertebral magnification factor relative to a selected vertebral centerline in the course of obtaining said lateral scan image.

5. A method as in claim 4 in which the imaging step comprises maintaining matching vertebral magnification factors in the course of obtaining both the AP and lateral scan images.

6. A method as in claim 5 in which said maintaining a constant vertebral magnification factor in the course of obtaining said lateral image comprises maintaining a constant distance between a source of the penetrating radiation and a selected vertebral centerline.

7. A method as in claim 6 in which the displaying step comprises displaying said AP and lateral images side-by-side and said utilizing step comprises carrying out computer-assisted but operator-controlled marking of significant points on the displayed lateral image.

8. A method as in claim 7 in which the utilizing step comprises maintaininq the respective cursors on said AP and lateral images coupled with each other such that one automatically follows movement of the other along an image.

9. A method as in claim 8 in which the imaging step comprises imaging the patient with said penetrating radiation for a period of time longer than 60 seconds in the course of obtaining said lateral scan image.

10. A method as in claim 9 in which the imaging step comprises imaging the patient with said penetrating radiation over a shorter time period to obtain the AP image than to obtain the lateral image.

11. A method as in claim 10 in which the imaging step comprises imaging the patient with a fan beam of penetrating radiation which in the course of obtaining said lateral image maintains an orientation in which one of the boundaries of the fan is horizontal.

12. A method as in claim 3 in which said imaging step comprises maintaining a constant vertebral magnification factor by maintaining a constant distance between a source of the penetrating radiation and a selected vertebral centerline.

13. A method as in claim 3 in which the displaying step comprises displaying said AP and lateral images side-by-side and said utilizing step comprises carrying out computer-assisted but operator-controlled marking of anatomically significant points on the displayed lateral image.

14. A method as in claim 13 in which the utilizing step comprises maintaining the respective cursors on said AP and lateral images coupled with each other such that one automatically follows movement of the other along an image.

15. A method as in claim 3 in which the imaging step comprises imaging the patient with said penetrating radiation for a period of time greater than of 60 seconds in the course of obtaining said lateral scan image.

16. A method as in claim 3 in which the imaging step comprises imaging the patient with said penetrating radiation over a shorter time period to obtain the AP image than to obtain the lateral image.

17. A method comprising the steps of:
   imaging a patient with penetrating radiation to obtain paired vertebral AP (anterior/posterior or posterior/anterior) and lateral scans, at least one of said AP and lateral scans being obtained by imaging the patient with dual energy penetrating radiation; and
   utilizing said paired scans to carry out computer-assisted vertebral morphometric analysis comprising manual designation by. an operator of the locations of at least a plurality of morphometrically significant points on a lateral image resulting from said lateral scan.

18. A method comprising the steps of:
   imaging a patient with a fan beam of penetrating radiation to obtain an AP (anterior/posterior or posterior/anterior) scan and a lateral scan of lumbar and thoracic vertebrae, wherein said lateral scan is obtained at a selected constant vertebral magnification relative to a selected vertebral centerline; and
   utilizing both of said AP and lateral scans to carry out computer-assisted vertebral morphometric analysis comprising manual designation by an operator of morphometrically significant points on at least one vertebra on at least one image obtained from said scans.

19. A method comprising the steps of:
   imaging a patient with penetrating radiation to obtain paired vertebral AP /anterior/posterior or posterior/anterior) and lateral scans while maintaining a selected constant distance between a source of the radiation and a vertebral centerline in the course of at least one of said AP and lateral scans; and
   utilizing said paired scans to carry out computer-assisted vertebral morphometric analysis.

20. A method comprising the steps of:
   imaging a patient with a fan beam of penetrating radiation to obtain one each of an AP (anterior/posterior or posterior/anterior) scan and a lateral scan of both lumbar and thoracic vertebrae while maintaining a selected constant fan beam magnification of the vertebrae during the lateral scan relative to a selected vertebral centerline; and
   utilizing both of said AP and lateral scans to carry out computer-assisted morphometric analysis of said vertebrae comprisinq the step of operator placement of selected cursor points for at least one vertebra on an image from said lateral scan.

21. A method comprising the steps of:
   carrying out a first examination of an individual with penetrating radiation to obtain first AP (anterior/posterior or posterior/anterior) and lateral scans thereof;
   utilizing said first AP and lateral scans to carry out a first computer-assisted vertebral morphometric analysis;
   carrying out a follow up examination of the individual with penetrating radiation to obtain follow up AP and lateral scans at a magnification of said vertebrae for at least the lateral scan which is the same as in said first examination;
   utilizing said follow up AP and lateral scans to carry out a follow up computer-assisted vertebral morphometric analysis; and identifying changes between said first and follow up examinations on the basis of at least some of said first and follow up scans and said first and follow up vertebral morphometric analysis.

22. A method comprising the steps of:

displaying side-by-side AP (anterior/posterior or posterior/anterior) and lateral scans of both lumbar and thoracic vertebrae of a patient imaged with penetrating radiation, and utilizing the side-by-side display to help identify vertebrae and to visualize spatial relationships of anatomy and pathology between said AP and lateral images which are displayed side-by-side; and carrying out computer-assisted vertebral morphometric analysis utilizing both of said AP and lateral scans.

23. A method comprising the steps of:

imaging a patient with penetrating radiation to obtain both an AP and a lateral scan of both lumbar and thoracic vertebrae;

said imaging for at least said lateral scan being carried out at an intensity of the penetrating radiation which is so low as to require in excess of 60 seconds to complete said lateral scan; and utilizing both of said AP and lateral scans to carry out computer-assisted morphometric analysis of said vertebrae to calculate at least posterior, mid- and anterior vertebral heights and vertebral wedge indices for at least selected ones of said vertebrae.

24. A method comprising the steps of:

imaging a patient with a fan beam of penetrating radiation to obtain both an AP (anterior/posterior or posterior/anterior) and a lateral scan of vertebrae;

said fan beam having a centerline and an angle between the beam boundaries, and said imaging to obtain said lateral scan being carried out with said fan centerline being at an angle relative to the horizontal of no less than half the angle between the beam boundaries; and utilizing both of said AP and lateral scans to carry out computer-assisted vertebral morphometric analysis in which an operator manually designates through a computer interface device significant vertebral points for at least one vertebra of at least the lateral image.

25. A method comprising the steps of:

imaging a patient with a fan beam of penetrating radiation to obtain paired AP (anterior/posterior or posterior/anterior) and lateral scan images, at least one of said paired images being obtained with dual energy penetrating radiation; and utilizing said paired images to determine a curve connecting anterior points of the lateral vertebral image and to derive a Kyphosis index related to the ratio of a deviation of the thoracic curve from a line connecting the lower anterior point of vertebrae T4 (thoracic 4) and L4 (lumbar 4) and the distance from the lower anterior point of vertebra T4 and the intersection of the curve with a polynomial fit.

26. A system comprising:

a bone densitometer imaging a patient with a fan beam of penetrating radiation to obtain paired AP (anterior/posterior or posterior/anterior) and lateral scan vertebral images, at least one of the paired images being obtained with dual energy penetrating radiation;

a display for side-by-side display of said images showing spatially synchronized movable cursors pointing at all times at anatomically corresponding portions of the AP and lateral images to help identify vertebrae and to help visualize spatial relationships of anatomy and pathology between said AP and lateral images which are displayed side-by-side; and a processor coupled with the display and responsive to the designation of points on the lateral image, including the manual designation and/or confirmation of points by an operator, to carry out vertebral morphometric analysis.

* * * * *